United States Patent
Trask et al.

(10) Patent No.: US 6,719,772 B2
(45) Date of Patent: Apr. 13, 2004

(54) RETAINING DEVICE FOR AXIALLY RESTRAINING MOVEMENT BETWEEN TUBULAR ELEMENTS OF A MEDICAL DEVICE

(75) Inventors: Linda Trask, Newark, DE (US); Philip A. Smith, Perryville, MD (US)

(73) Assignee: Terumo Medical Corporation, Somerset, NJ (US)

( * ) Notice: Subject to any disclaimer, the term of this patent is extended or adjusted under 35 U.S.C. 154(b) by 203 days.

(21) Appl. No.: 09/950,656

(22) Filed: Sep. 13, 2001

(65) Prior Publication Data

US 2003/0050658 A1 Mar. 13, 2003

(51) Int. Cl.$^7$ .............................................. A61M 29/00
(52) U.S. Cl. ................ 606/191; 604/164.1; 604/165.03
(58) Field of Search ..................... 604/165.03, 165.04, 604/165.01, 165.02, 164.1; 606/191, 108

(56) References Cited

U.S. PATENT DOCUMENTS

| 3,479,069 A | 11/1969 | Sedam |
| 3,672,367 A | 6/1972 | Scislowicz |
| 3,769,975 A | 11/1973 | Nimoy et al. |
| 3,930,674 A | 1/1976 | Jonsson |
| 4,079,738 A | 3/1978 | Dunn et al. |
| 4,082,094 A | 4/1978 | Dailey |
| 4,149,535 A | 4/1979 | Volder |
| 4,233,974 A | 11/1980 | Desecki et al. |
| D271,904 S | 12/1983 | Tucker |
| 4,493,708 A | 1/1985 | Sugisawa |
| 4,496,348 A | 1/1985 | Genese et al. |
| 4,539,003 A * | 9/1985 | Tucker .................... 604/93.01 |
| 4,540,411 A | 9/1985 | Bodicky |
| D283,441 S | 4/1986 | Vcelka et al. |
| 4,629,450 A * | 12/1986 | Suzuki et al. ............ 604/164.1 |
| 4,643,389 A | 2/1987 | Elson et al. |
| 5,064,414 A * | 11/1991 | Revane .................. 604/165.01 |
| 5,092,846 A * | 3/1992 | Nishijima et al. ...... 604/167.04 |
| 5,242,410 A * | 9/1993 | Melker .................... 604/164.1 |
| 5,250,036 A | 10/1993 | Farivar |
| 5,437,643 A | 8/1995 | Transue |
| 5,584,816 A | 12/1996 | Gyure et al. |
| 5,957,894 A | 9/1999 | Kerwin et al. |
| D431,650 S | 10/2000 | Guala et al. |
| 2002/0007152 A1 * | 1/2002 | Hermann et al. ....... 604/167.04 |

FOREIGN PATENT DOCUMENTS

WO    WO 93/13817 A1    7/1993

\* cited by examiner

Primary Examiner—Michael J. Milano
Assistant Examiner—D. Jacob Davis
(74) Attorney, Agent, or Firm—Burns, Doane, Swecker & Mathis, L.L.P.

(57) ABSTRACT

A retaining device for axially restraining a sheath connected to a housing and a dilator connected to a hub includes a generally C-shaped clip having spaced apart circumferential ends defining a clearance opening that opens into the clip interior to permit the clip to be mounted on the hub and an enlarged part of the housing. The interior of the clip has first and second inwardly directed ridges located at opposite axial portions of the curved inner circumferential surface for overlapping portions of oppositely facing end surfaces of the hub and the enlarged part of the housing. The clip also includes one or more laterally outwardly extending finger engaging tabs to facilitate removal of the clip, and one or more circumferentially extending through slot communicating the inner surface of the clip with an outer surface of the clip to permit flexing of the clip during removal of the clip.

23 Claims, 5 Drawing Sheets

RETAINING DEVICE FOR AXIALLY RESTRAINING MOVEMENT BETWEEN TUBULAR ELEMENTS OF A MEDICAL DEVICE

FIELD OF THE INVENTION

This invention generally relates to a retaining device for restraining movement between two parts of a medical instrument. More particularly, the present invention pertains to a retaining clip for axially restraining movement between a dilator and a sheath forming part of a sheath assembly.

BACKGROUND OF THE INVENTION

Some types of medical procedures that require intervention into a patient's blood vessel for purposes of accessing a desired site (e.g., carotid artery) so that a medical procedure can be carried out involve the use of a guiding sheath. Once in place within the patient's vessel, various types of medical instrumentation (e.g., a balloon catheter) can be fed through a lumen in the sheath and positioned at the desired site.

To initially gain access to a particular site within a patient, a needle is used to puncture the patient's skin and gain entry to a desired blood vessel. A guide wire is then inserted into a lumen in the needle and is fed into the blood vessel. The needle is removed, with the guide wire being left in place. The tip of a sheath assembly, which includes a sheath, is then placed over the guide wire and advanced to a position inside the blood vessel. The guide wire is then advanced within the blood vessel to the desired site, followed by advancement of the sheath assembly to the desired location. Once the sheath assembly is in place at the desired site, the sheath can be used to introduce and guide medical instrumentation to the desired site within the blood vessel.

However, because the sheath is typically used as a mechanism for guiding medical instrumentation into a blood vessel, the sheath possesses a relatively large diameter. Inserting this relatively large diameter sheath into the patient without any special provision could cause trauma, injury or other difficulties to the patent. To avoid such difficulties, the sheath assembly typically includes a tubular dilator that is generally coaxially disposed within the tubular sheath. The distal end of the dilator is tapered to a relatively small diameter and extends beyond the distal end of the tubular sheath which may be formed so that it is also slightly tapered. A smooth transition is thus presented between the tapered distal end of the dilator and the distal end of the sheath. The tapered distal end of the dilator allows the dilator/sheath assembly to be introduced into a patient's vessel in a manner that gradually increases the size of the opening into the vessel so that the vessel can ultimately accommodate the larger sized sheath without causing potential trauma, injury or other difficulties to the patient.

To achieve the desired gradual increase in the size of the opening into the vessel, the smooth transition between the tapered distal end of the dilator and the distal end of the sheath must be maintained during the use of the dilator/sheath assembly. This necessitates that axial movement between the dilator and the sheath be restrained during use of the dilator/sheath assembly. If the dilator is axially retracted within the sheath, the relatively large and somewhat blunt end of the sheath will be exposed and could cause the aforementioned undesirable trauma or injury to the patient.

Various proposals have been made for devices adapted to be used in connection with medical instruments for securing two elongated members relative to one another in a way that inhibits relative axial movement. For example, U.S. Pat. No. 5,064,414 discloses a locking clip for placement between a dilator and sheath. Although this clip may be able to secure the dilator and sheath relative to one another to inhibit relative axial movement, the construction of the locking clip is somewhat complicated and requires that the sheath with which it is used possess tabs for engagement by the locking clip. Further, the disclosed locking clip does not lend itself to being easily removed so that the dilator can be withdrawn fro the sheath once the dilator/sheath assembly is properly positioned within the vessel.

U.S. Pat. No. 4,233,974 discloses a bridging member specifically adapted for use in a spinal needle assembly to prevent the obturator stylet from axially moving relative to the cannula. This bridging member, although possibly useful in the context of a spinal needle assembly, is not particularly well suited for use in other contexts such as a dilator/sheath assembly. For example, in the case of the disclosed spinal needle assembly, the aforementioned patent describes that it the obturator and the cannula must be secured to one another in a way that prevents rotational movement of the obturator relative to the stylet. In the case of a dilator/sheath assembly, similar concerns about prohibiting rotational movement between the dilator and the sheath may not exist. In fact, in at least some applications, the guiding sheath is connected to a housing containing a hemostatic valve that is operable by way of a rotatable cap. With this construction, any type of device for axially restraining the sheath and dilator relative to one another should be designed so that when the device is in use, the cap is still capable of being rotated to effect operation of the hemostatic valve. In addition, in the case of a dilator/sheath assembly used in the manner described above, a device for axially restraining relative movement between the sheath and dilator should be designed to permit access to the lumen in the dilator. The spinal needle assembly locking clip disclosed in the aforementioned U.S. Pat. No. 4,233,974 is also not particularly well suited for being easily positioned in place and then subsequently removed.

A need thus exists for a retaining device that can be used with, for example, a sheath/dilator assembly which requires rotation of a cap to effect operation of a hemostatic valve.

A need also exists for a dilator/sheath assembly retaining device that is relatively uncomplicated in construction, yet can be readily mounted in place and subsequently removed without significant difficulty.

SUMMARY OF THE INVENTION

According to one aspect of the invention, a sheath assembly includes a tubular dilator, a tubular sheath and a retaining device. The dilator has a tapered distal end and possesses a lumen, and is connected to a hub. The sheath has a distal end and possesses a lumen, and is the connected to a housing provided with a hemostatic valve and a rotatable cap that is operatively associated with the hemostatic valve for operating the valve upon rotation of the cap. The dilator extends through the hemostatic valve and through the lumen of the sheath, with the tapered distal end of the dilator extending beyond the distal end of the sheath. The retaining device includes a clip surrounding circumferential portions of the hub and the cap as well as portions of oppositely facing end surfaces of the hub and the cap to restrain axial movement between the hub and the cap. The clip also has an inner surface shaped to permit rotation of the cap to operate the hemostatic valve.

Another aspect of the invention involves a retaining device for axially restraining movement between a tubular sheath connected to a housing provided with a rotatable cap and a tubular dilator connected to a hub and extending through a lumen in the housing and the sheath. The retaining device includes a generally C-shaped clip having spaced apart circumferential ends defining a clearance opening that opens into an interior of the clip to permit the clip to be mounted in a partial circumferentially surrounding relationship on the hub of the dilator and the cap of the housing. The interior of the clip has a curved inner circumferential surface to permit rotation of the rotatable cap when the clip is mounted on the hub of the dilator and the cap of the housing. The interior of the clip has first and second axially spaced apart and inwardly directed ridges located at opposite axial portions of the curved inner circumferential surface for overlapping with portions of oppositely facing end surfaces of the cap and the hub when the clip is mounted on the hub and the cap. The clip also includes at least one laterally outwardly extending finger engaging tab positioned adjacent one of the circumferentially spaced apart ends of the clip to facilitate removal of the clip from the hub and cap. The clip is also provided with at least one circumferentially extending through slot communicating the inner surface of the clip with an outer surface of the clip to permit flexing of the clip during removal of the clip from the hub and cap.

In accordance with another aspect of the invention, a retaining device for restraining axial movement between a tubular sheath, connected to a housing having an enlarged part, and a tubular dilator, connected to a hub and extending through a lumen in the housing and the sheath, includes a clip having an interior bounded by an inner circumferential surface of the clip, with the clip having spaced apart circumferential ends between which is defined a clearance opening that opens into the interior of the clip for allowing the clip to be mounted on the hub and the enlarged part of the housing, and with the clip also having an opening at each axial end of the clip, the interior of the clip defining first and second interior portions positioned axially adjacent one another. The first interior portion is adapted to receive and circumferentially surround a portion of the hub while the second interior portion is adapted to receive and circumferentially surround a portion of the enlarged part of the housing, with the first and second interior portions of the clip being of different size.

According to a further aspect of the invention, a retaining device for restraining axial movement between a tubular sheath, connected to a housing having an enlarged part, and a tubular dilator, connected to a hub and extending through a lumen in the housing and the sheath, includes a clip having an interior bounded by an inner circumferential surface of the clip, with the clip having spaced apart circumferential ends defining a clearance opening that opens into the interior of the clip for allowing the interior of the clip to receive portions of the hub and the enlarged part of the housing, and with the clip including at least one laterally outwardly extending finger engaging tab extending laterally outwardly from adjacent one of the circumferential ends of the clip for being engaged by an individual's finger to facilitate removal of the clip from the hub and the enlarged part of the housing.

BRIEF DESCRIPTION OF THE DRAWING FIGURES

The foregoing and additional features and characteristics of the present invention will become more apparent from the following detailed description considered with reference to the accompanying drawing figures in which like elements are designated by like reference numerals and wherein.

DETAILED DESCRIPTION OF THE INVENTION

Figure 1:
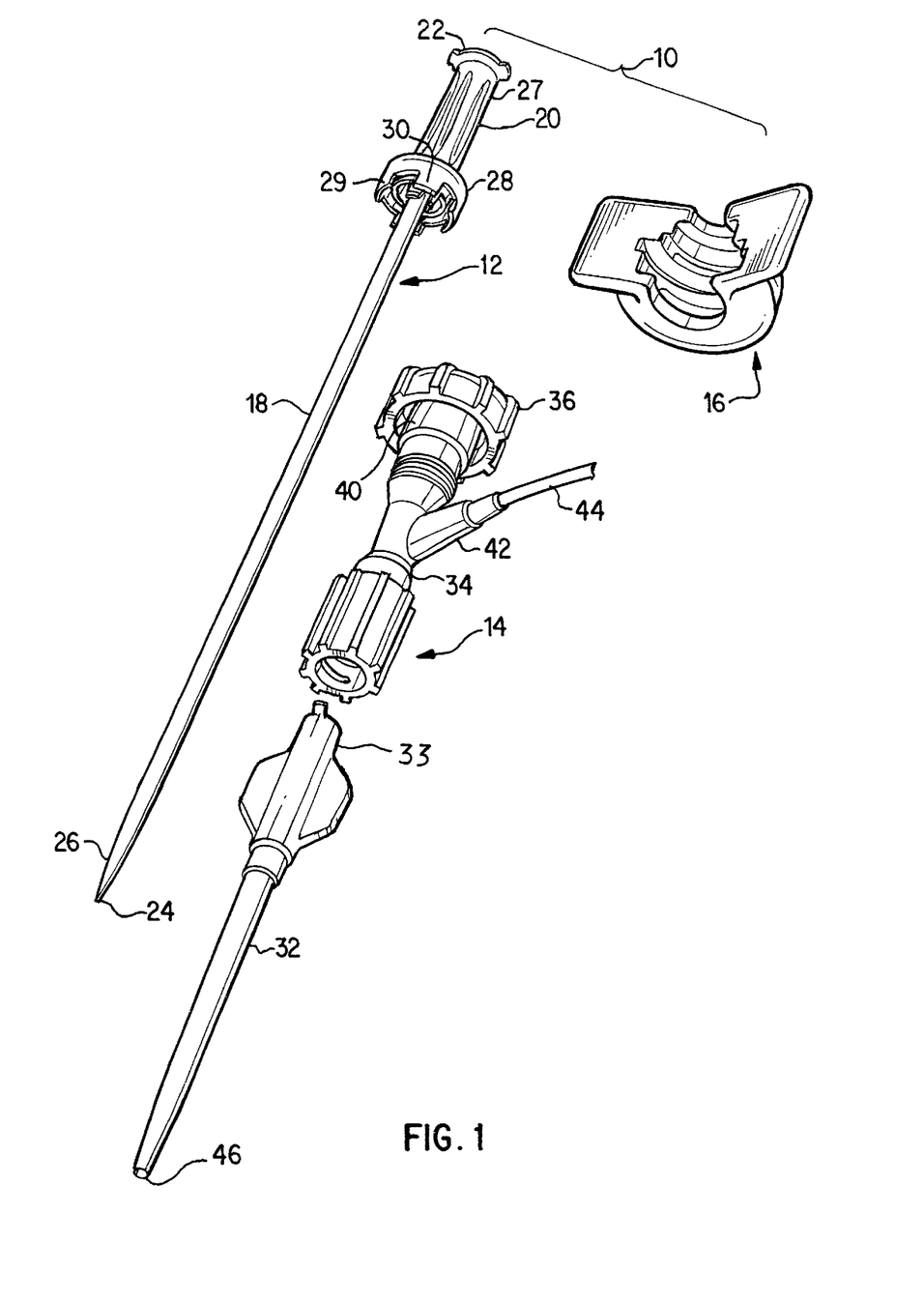
FIG. 1 is a perspective view of various parts forming the sheath assembly of the present invention.
Figure 2:
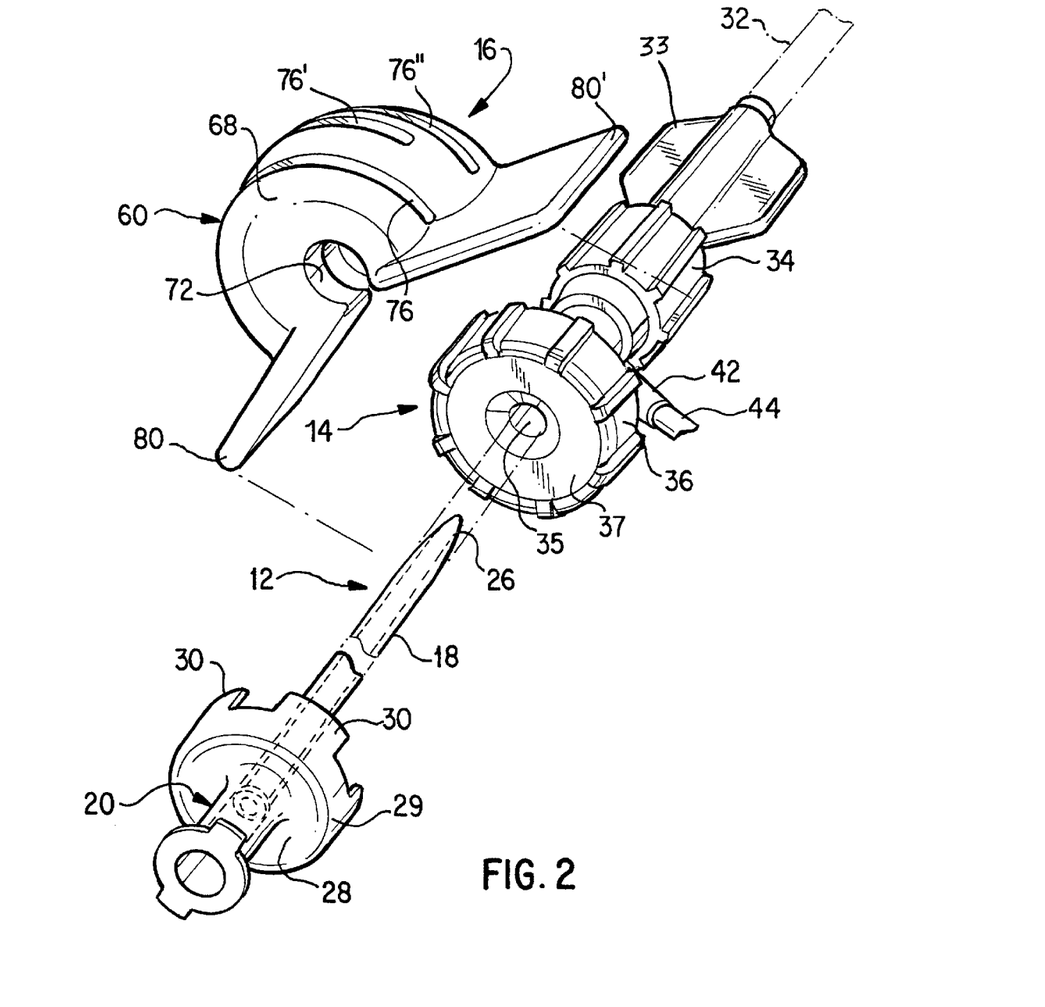
FIG. 2 is a rear perspective view illustrating the way in which the dilator is inserted into the housing of the sheath device prior to attachment of the retaining device.
Figure 3:
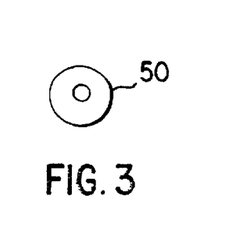
FIG. 3 is a top view of a hemostatic valve used in the sheath assembly shown in FIG. 1, with the hemostatic valve being in an open position.

The present invention provides a retaining device which, in one respect, can be used for restraining axial movement between a sheath and a dilator. The retaining device is particularly useful in restraining axial movement of a sheath and a dilator that also includes a rotatable valve. FIGS. 1–3 illustrate a sheath assembly that includes the retaining device of the present invention.

The sheath assembly 10 is comprised of a dilator device 12, a sheath device 14 and the retaining device 16. The dilator device 12 is comprised of an elongated tubular dilator 18 and a hub 20. The dilator 18 and the hub 20 are fixedly secured to one another in a manner that prevents axial and rotational movement of the dilator 18 relative to the hub 20. Both the dilator 18 and the hub 20 are provided with a centrally extending lumen, with the lumen in the dilator 18 communicating with the lumen in the hub 20. The lumen in the hub 20 is open at the proximal end 22 of the hub 20 while the lumen in the dilator 18 opens to the distal end 24 of the dilator 18. Thus, a lumen extends completely through the dilator device 12 and opens to the outside at opposite ends of the dilator device 12. In addition, as can be seen from FIG. 1, the distal end portion 26 of the dilator 18 is tapered so that the outer diameter of the dilator 18 gradually narrows towards the distal end 24 of the dilator 18.

The hub 20 that is connected to the proximal end of the dilator 18 is provided with a lower enlarged part 29 extending outwardly from a cylindrical upper portion 27 as shown in FIG. 1. The enlarged part 29 of the hub 20 is defined by a radially outwardly directed ledge 28 and several projections 30 extending axially from the ledge 28 in a direction away from the proximal end 22 of the hub 20.

The sheath device 14 includes an elongated tubular sheath 32, a housing 34 and a cap 36. The sheath 32 can be removably secured to the housing 34 by way of a fitting 33 provided at the proximal end of the sheath 32. The connection between the fitting 33 and the housing 34 can be achieved using a known luer lock connection.

The proximal end portion of the housing 34 is provided with an externally threaded portion 40 that is threadably engaged by internal threads on the cap 36. The cap 36 can thus be rotated relative to the housing 34, but is preferably designed to prevent the cap 36 from being completely separated from the housing 34. That is, a catch is built into the cap 36 to prevent the cap from coming off the housing 34. The housing 34 is also provided with an integrally formed branch port 42 connected to a tubing 44. The tubing 44 can be connected to a three-way stop cock to allow fluids to be injected into or withdrawn from the patient during the procedure. For example, the tubing and the stop cock can be used to sample blood or inject a contrast medium or agent.

The elongated sheath 32 and the housing 34 are both provided with respective lumens that communicate with one another. The tubing 44 also communicates with the lumen in the housing 34. The lumen in the housing 34 opens to the proximal end of the housing 34 while the lumen in the sheath 32 opens to the distal end 46 of the sheath 32.

Figure 4:
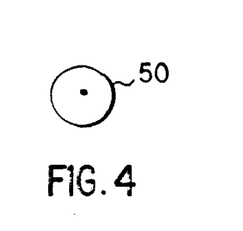
FIG. 4 is a top view of the hemostatic valve shown in FIG. 3 in a closed position.

In a manner known in the art, the housing 34 is provided with a hemostatic valve 50 generally illustrated in FIG. 3 and known in the art. Generally speaking, the hemostatic valve 50 is in the form of a cylindrical plastic element having a generally centrally located through hole. The hemostatic valve 50 is positioned within a chamber in the housing 34 and the rotatable cap 36 is operatively associated with the hemostatic valve 50. That is, by rotating the cap 36 so that the cap moves axially with respect to the housing 34 in a direction towards the elongated sheath 32, an internal portion of the cap engages the cylindrical element forming the hemostatic valve 50 and thus compresses the cylindrical element causing the through hole in the cylindrical member to be closed as shown in FIG. 4. Thus, by suitably rotating the cap 36 on the housing 34, the hemostatic valve 50 can be moved between the opened position shown in FIG. 3 and the closed position shown in FIG. 4. The hemostatic valve 50 can be used to prevent blood loss during a procedure involving use of the sheath assembly by providing a tight seal around the outer surface of the dilator 18. The hemostatic valve 50 also allows dilators of different sizes and profiles to pass through the hemostatic valve.

As can be seen from FIG. 2, the elongated sheath 18 is adapted to be inserted into the lumen 35 in the housing 34 and then advanced so that the elongated sheath 18 extends through the lumen 35 in the housing 34 as well as through the lumen in the elongated sheath 32. In the assembled state shown in FIG. 5, the ends of the projections 30 extending from the ledge 28 of the hub 20 contact the recessed end surface 37 of the cap 36. In addition, the tapered distal end portion 26 of the dilator 18 extends beyond the distal end 46 of the elongated sheath 32 such that a smooth transition exists between the tapered distal end portion 26 of the dilator 18 and the distal end portion 48 of the sheath 32. In this regard, the distal end portion 48 of the sheath can be configured as a formed tip (e.g., having a slightly tapered end) to further facilitate the smooth transition between the tapered distal end portion 26 of the dilator 18 and the distal end portion 48 of the sheath 32.

Figure 6:
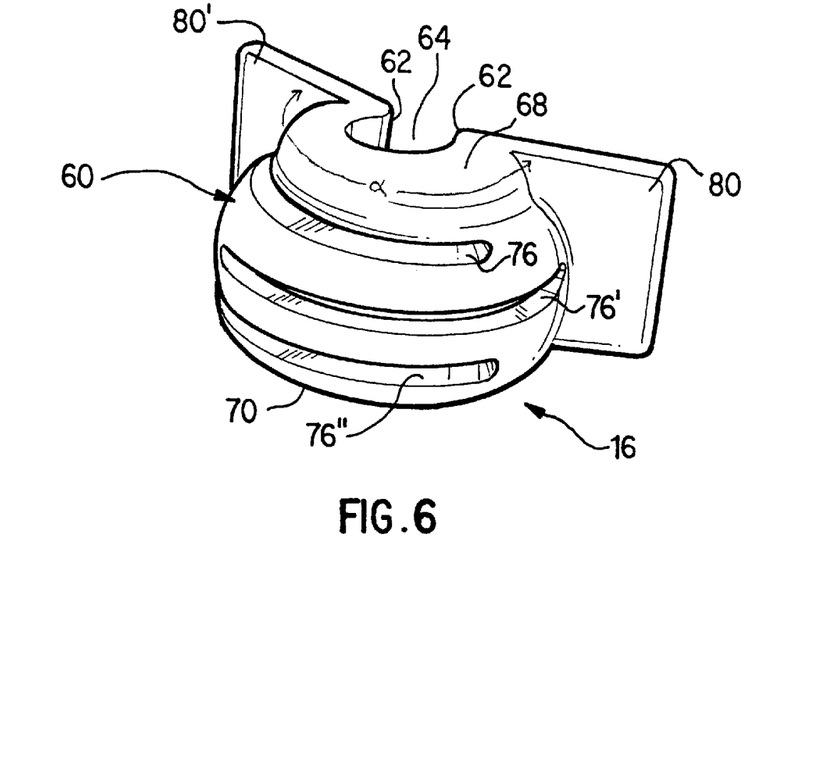
FIG. 6 is a rear perspective view of the retaining device used in the sheath assembly of the present invention.
Figure 7:
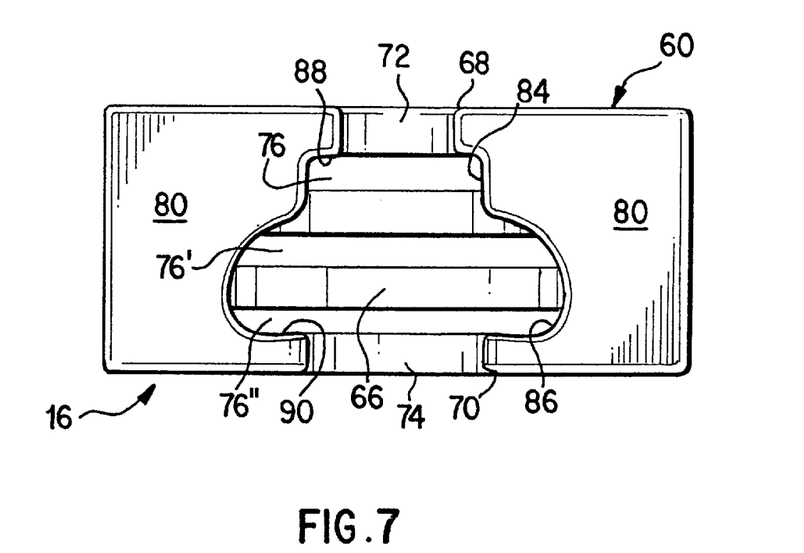
FIG. 7 is a front plan view of the retaining device illustrated in FIG. 4.

As seen with particular reference to FIGS. 6 and 7, the retaining device 16 forming a part of the guiding sheath assembly 10 is in the form a generally C-shaped retaining clip 60. The retaining clip 60 is configured to define two circumferential ends 62, 62 that are circumferentially spaced apart from one another to define a clearance opening 64 that opens into the interior 66 of the retaining clip 60. This clearance opening 64 allows the interior of the clip to receive portions of the sheath hub 20 and the dilator housing cap 36. The retaining clip 60 is also provided with oppositely located end walls 68, 70, each provided with a respective through hole or opening 72, 74 that opens into the interior 66 of the retaining clip 60. As can be readily seen from FIG. 7, the through hole or opening 72 at the upper axial end wall of the retaining clip 60 is smaller in size (e.g., diameter) than the through hole or opening 74 at the lower axial end wall of the retaining clip 60.

As illustrated in FIG. 6, the exterior surface of the retaining clip 60 is smoothly curved along its entire circumferential extent. This configuration facilitates placement and removal of the retaining clip with respect to the sheath device and the dilator device, thus providing a more user-friendly retaining device.

The retaining device 60 is preferably made from a plastic material. Through the use of plastic material, a certain degree of flexibility is imparted to the retaining device 60, thus facilitating attachment and removal of the retaining device. One type of plastic material which can be employed is LDPE, although other materials can also be employed.

In addition, as seen in FIG. 6, the retaining clip 60 is provided with a plurality of circumferentially extending through slots 76, 76', 76". The through slots 76, 76', 76" extend completely through the retaining clip and thus open to the outer circumferential surface of the retaining clip 60 as well as to the inner circumferential surface of the retaining clip 60. These through slots 76, 76', 76" impart an added degree of flexibility to the retaining device to facilitate the attachment and removal of the retaining device 60 with respect to the dilator hub 20 of the dilator device 12 and the housing cap 36 of the sheath device 14. In the illustrated embodiment, the clip 60 is provided with three axially spaced apart through slots 76, 76', 76" defining an upper through slot 76, a lower through slot 76" and an intermediate through slot 76'. Of course, a different number of through slots may be employed depending upon the desired degree of flexibility and other factors such as the material from which the clip is made, the wall thickness of the clip, etc.

In addition, as can be readily seen from FIGS. 2 and 6, the axially adjacent through slots 76, 76', 76" are partially circumferentially offset or shifted with respect to one another. That is, one end portion of the intermediately located through slot 76' extends circumferentially beyond the adjacent end portions of the upper and lower through slots 76, 76". Similarly, the opposite end portions of the upper and lower through slots 76, 76" extend circumferentially beyond the adjacent end portion of the intermediately located through slot 76'. With this partial circumferential offsetting or shifting of the through slots, a desired degree of flexibility can be imparted to the retaining clip 60 without undesirably compromising the necessary strength of the retaining clip 60 and without resulting in an excessive degree of flexing.

The retaining clip 60 is also provided with a pair of finger engaging tabs 80, 80'. These finger engaging tabs 80, 80' extend laterally outwardly from a position adjacent each of the circumferential ends 62, 62 of the retaining clip 60. These finger engaging tabs 80, 80' extend laterally outwardly at approximately 90° with respect to the adjoining outer circumferential surface of the retaining clip 60, and provide a surface against which the user can press when removing the retaining clip, thereby facilitating removal of the retaining clip 60.

As can be seen from FIG. 7, the interior 66 of the retaining clip 60 includes a first interior portion 84 (upper interior portion) and a second interior portion 86 (lower interior portion) that axially adjoin one another. The first interior portion 84 possesses a size (e.g., a radius) that is smaller than the second interior portion 86. The smaller first interior portion is positioned adjacent the through opening 72 in the upper axial end wall 68 of the retaining clip 60 while the larger second interior portion 86 is positioned adjacent the through opening 74 in the bottom axial end wall 70 of the retaining clip 60. In addition, the smaller first interior portion 84 smoothly merges into the larger second interior portion 86 in the manner illustrated in FIG. 7.

The interior of the retaining clip 60 is also configured to define two axially spaced apart ridges 88, 90. One of the ridges 88 is located at the upper end of the interior 66 of the retaining clip adjacent the opening 72 in the upper axial end wall 68 of the retaining clip 60 while the other ridge 90 is located at the opposite axial end or lower end of the interior 66 adjacent the opening 74 in the bottom axial end wall of the retaining clip 60. The ridge 88 is adapted to overlie and surround a portion of the upwardly facing upper end face of the ledge 28 of the hub 20, while the other ridge 90 is adapted to underlie and surround a portion of the downwardly facing lower surface of the cap 36.

To assemble the guiding sheath assembly 10, the elongated sheath 18 is inserted into the open end of the housing as shown in FIG. 2. The elongated sheath 18 is then advanced so that the elongated sheath 18 extends through the lumen 35 in the housing 34 as well as through the lumen in the elongated sheath 32. In the assembled state shown in FIG. 5, the tapered distal end portion 26 of the dilator 18 extends beyond the distal end 46 of the elongated sheath 32 such that a smooth transition exists between the tapered distal end portion 26 of the dilator 18 and the tapered distal end portion 48 of the sheath 32.

Figure 5:
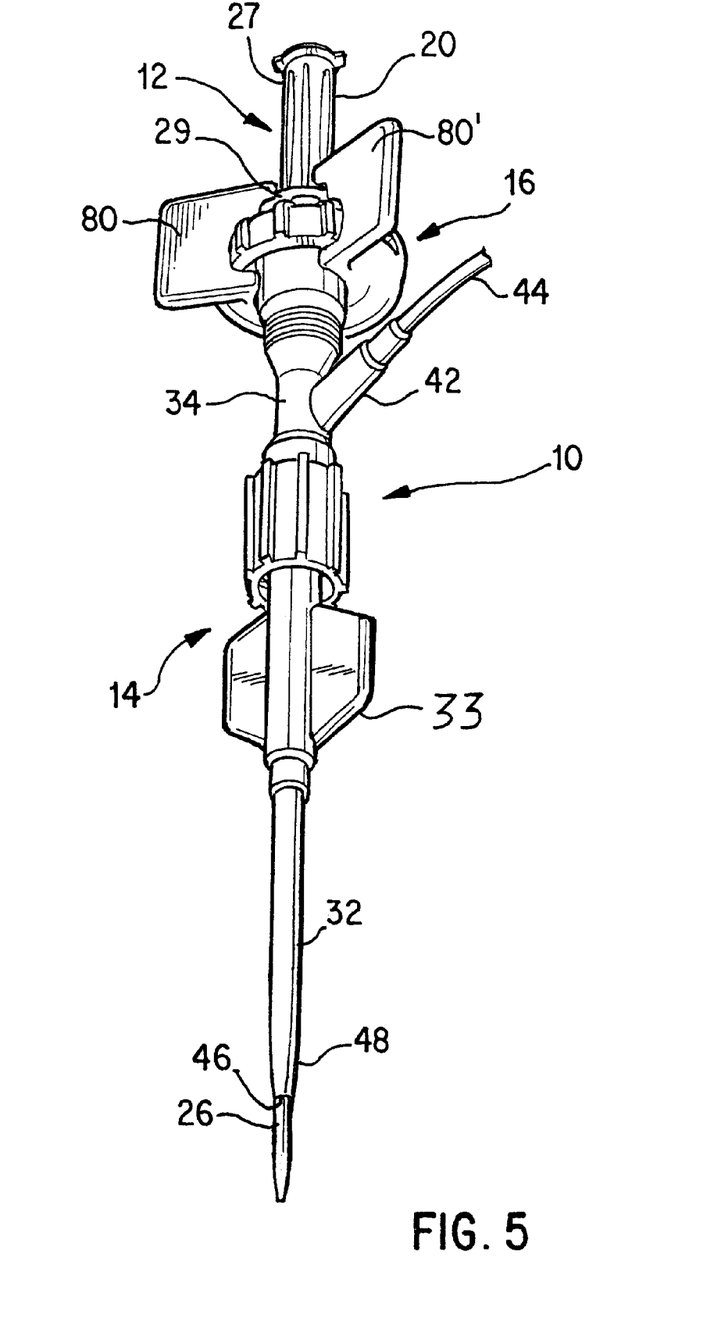
FIG. 5 is a lower perspective view of the sheath assembly in the assembled state.
Figure 8:
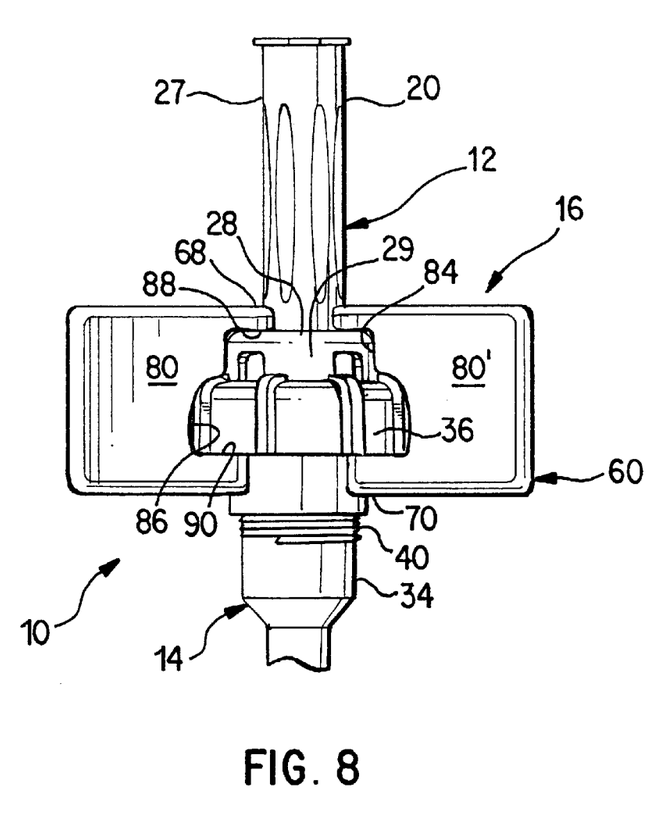
FIG. 8 is a front view of a portion of the sheath assembly illustrated in FIG. 3.

The retaining clip 60 is then mounted on the hub 20 of the dilator device 12 and the cap 36 of the sheath housing 34 in the manner illustrated in FIG. 8. This mounting of the retaining clip 60 can be accomplished by positioning the retaining clip 60 so that the enlarged part 29 of the hub 20 and the cap 36 are generally aligned with the first and second interior portions 84, 86 of the retaining clip 60, respectively, in the region of the circumferential clearance opening 64 of the retaining clip 60. The retaining clip 60 can then be pressed towards the enlarged portion 29 of the hub 20 and the cap 36 to snap the retaining clip 60 in place as shown in FIGS. 5 and 8. As the retaining clip 60 is snapped in place, portions of the retaining clip located between the through slots 76, 76', 76" are able to slightly flex or deform to allow the retaining clip 60 to be more easily mounted in place.

As can be seen from FIG. 8, when the clip 60 is snapped onto the enlarged part of the hub 20 and the cap 36, the smaller first interior portion 84 of the retaining clip 60 receives and circumferentially surrounds a portion of the enlarged part 29 of the hub 20, with the ridge 88 surrounding and overlying a portion of the upwardly facing end surface of the ledge 28. In addition, the larger second interior portion 86 of the retaining clip 60 receives and circumferentially surrounds a portion of the cap 36, with the second ridge 90 surrounding and underlying a portion of the downwardly facing or lower surface of the cap 36.

As can also be seen from FIG. 8, when the retaining clip 60 is mounted in place, the upper end 27 of the hub 20 extends out through the opening 72 in the upper axial end wall 68 of the retaining clip 60 while the lower portion of the housing 34 extends out through the opening 74 in the bottom axial end wall 70 of the retaining clip 60. Thus, the lumen in the hub 20 that communicates with the lumen in the elongated sheath 18 can be accessed when the retaining clip 60 is in the mounted condition shown in FIG. 8.

When the retaining clip 60 is mounted on the hub 20 and the cap 36 in the manner shown in FIGS. 5 and 8, the elongated dilator 18 (as well as the integrally connected hub 20) and the elongated sheath 32 (as well as the housing 34 and cap 36) are restrained from axially moving relative to one another. By axially restraining the elongated dilator 18 and the elongated sheath 32 in this manner, the tapered distal end portion 26 of the dilator 18 and the tapered distal end portion 48 of the sheath 32 are maintained in the position shown in FIG. 5 to ensure that a smooth transition exists between the tapered distal end portion 26 of the dilator 18 and the distal end portion 48 of the sheath 32 during insertion of the distal end portion of the assembly into a vessel during use.

In addition, as mentioned above, the inner circumferential surface of the retaining clip 60 is configured (e.g., curved) in a manner that allows the cap 36 to be rotated on the housing 34 when the retaining clip 60 is engaged with the cap 36 and the hub 20 in the manner shown in FIG. 8. In this way, the cap 36 can be rotated even when the retaining clip 60 is in the mounted condition. This provides freedom of usage when the retaining clip 60 is in the mounted condition and allows the hemostatic valve 50 to be operated as desired. In this way, the valve can be tightened about the dilator to prevent leakage, while at the same time allowing the valve to be loosened relative to the dilator prior to removing the dilator.

It is to be noted that the retaining clip 60 can be mounted on the enlarged part 29 of the hub 20 and the cap 36 in any circumferential position. That is, it is not necessary to rotationally orient the retaining clip 60 in any particular position relative to the hub 20 and the cap 36. Also, when the retaining clip 60 is in the mounted position, the retaining clip surrounds at least 180° of the circumferential extent of the enlarged part 29 of the hub 20 and the cap 36. In the illustrated embodiment of the invention, the retaining clip 60 is configured to surround 225° of the circumferential extent of the enlarged part 29 of the hub 20 and the cap 36 (i.e., the rotational angle α shown in FIG. 6 between the finger engaging tabs 80, 80' is 225°).

To use the sheath assembly assembled in the manner shown in FIG. 5, a needle is first used to puncture a patient's skin and gain access to the patient's blood vessel. Once access to the blood vessel has been gained with the needle, a guide wire is inserted into the needle and is positioned in the blood vessel. The needle can then be removed. The sheath assembly 10 (with the retaining clip 16 mounted as shown in FIG. 5 to axially restrain movement between the dilator device 12 and the sheath device 14) is then positioned over the guide wire, with the guide wire passing through the lumen in the dilator 18 and the hub 20. In this way, the sheath assembly can be introduced into the blood vessel. The guide wire is then fed to the desired site (or close to the desired site) within the blood vessel (e.g., carotid artery). The sheath assembly 10 is then advanced over the guide wire to the desired location.

During introduction of the sheath assembly into the blood vessel, the exposed tapered distal end portion 26 of the dilator 18 allows the size of the opening into the blood vessel to be gradually increased so that the blood vessel is ultimately able to accommodate the larger diameter size of the sheath 32. In addition, the smooth transition between the tapered distal end portion 26 of the elongated dilator 18 and the formed distal end portion 48 of the sheath 32 facilitates a smooth introduction of the distal end portion of the sheath assembly 10. Once the distal end of the elongated sheath 32 is located at the desired position in the vessel (e.g., by identifying the location of a radiopaque marker embedded within the distal end of the elongated sheath 32), the retaining clip 60 is removed, and the dilator device 12 comprised of the elongated dilator 18 and the hub 20 is axially withdrawn from the sheath assembly 14. The elongated sheath 32 and the guide wire are thus left in place in the blood vessel. The elongated sheath 32 can then be used, for example, as a guiding sheath or introducer for guiding or introducing various medical instrumentation (e.g., a balloon catheter) into the blood vessel at the desired site.

It is also possible to provide a tether between the retaining clip 60 and the hub 20, or between the retaining clip 60 and the housing 34. This thus provides a mechanism for connecting the retaining clip to another part of the assembly in the event it is necessary or desirable to temporarily separate the dilator assembly from the sheath assembly (e.g., to flush the sheath and/or the dilator).

The principles, preferred embodiment and mode of operation of the present invention have been described in the foregoing specification. However, the invention which is intended to be protected is not to be construed as limited to the particular embodiment disclosed. The embodiment described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A sheath assembly comprising:
a dilator having a tapered distal end and possessing a lumen, the dilator being connected to a hub;
a sheath having a distal end and possessing a lumen, the sheath being connected to a housing provided with a hemostatic valve and a rotatable cap that is operatively associated with the hemostatic valve for operating the valve upon rotation of the cap, the dilator extending through the hemostatic valve and through the lumen of the elongated sheath, with the tapered distal end of the dilator extending beyond the distal end of the sheath;
a retaining device comprising a clip surrounding circumferential portions of the hub and the cap as well as portions of oppositely facing end surfaces of the hub and the cap to restrain axial movement between the hub and the cap, the clip having an inner surface shaped to permit rotation of the cap to operate the hemostatic valve.

2. The sheath assembly according to claim 1, wherein the retaining clip is substantially C-shaped.

3. The sheath assembly according to claim 1, wherein the retaining clip is provided with a plurality of circumferentially extending elongated through slots.

4. The sheath assembly according to claim 3, wherein portions of adjacent ones of the through slots are circumferentially shifted relative to one another.

5. The sheath assembly according to claim 1, wherein the retaining clip is substantially C-shaped to define spaced apart circumferential ends of the retaining clip, the retaining clip having a pair of tabs each positioned adjacent one of the circumferential ends of the retaining clip and extending outwardly from the C-shaped retaining clip to provide a finger engaging portion facilitating removal of the retaining clip from the hub and the cap.

6. The retaining device according to claim 5, wherein the at least one finger engaging tab includes two laterally outwardly extending finger engaging tabs, each positioned adjacent one of the circumferential ends of the clip.

7. A retaining device for axially restraining movement between a tubular sheath connected to a housing provided with a rotatable cap and a tubular dilator connected to a hub and extending through a lumen in the housing and the sheath, the retaining device comprising:
a generally C-shaped clip having spaced apart circumferential ends defining a clearance opening that opens into an interior of the clip to permit the clip to be mounted in a partial circumferentially surrounding relationship on the hub of the dilator and the cap of the housing, the interior of the clip having a curved inner circumferential surface to permit rotation of the rotatable cap when the clip is mounted on the hub of the dilator and the cap of the housing, the interior of the clip having first and second axially spaced apart and inwardly directed ridges located at opposite axial portions of the curved inner circumferential surface for overlapping with portions of oppositely facing end surfaces of the cap and the hub when the clip is mounted on the hub and the cap, the clip including at least one laterally outwardly extending finger engaging tab positioned adjacent one of the circumferentially spaced apart ends of the clip to facilitate removal of the clip from the hub and cap, the clip including at least one circumferentially extending through slot communicating the inner surface of the clip with an outer surface of the clip to permit flexing of the clip during removal of the clip from the hub and cap, wherein the at least one circumferentially extending through slot includes a plurality of axially spaced apart through slots communicating the inner surface of the clip with the outer surface of the clip.

8. The retaining device according to claim 7, wherein portions of adjacent ones of the through slots are at least partially circumferentially shifted relative to one another.

9. A retaining device for axially restraining movement between a tubular sheath connected to a housing provided with a rotatable cap and a tubular dilator connected to a hub and extending through a lumen in the housing and the sheath, the retaining device comprising:
a generally C-shaped clip having spaced apart circumferential ends defining a clearance opening that opens into an interior of the clip to permit the clip to be mounted in a partial circumferentially surrounding relationship on the hub of the dilator and the cap of the housing, the interior of the clip having a curved inner circumferential surface to permit rotation of the rotatable cap when the clip is mounted on the hub of the dilator and the cap of the housing, the interior of the clip having first and second axially spaced apart and inwardly directed ridges located at opposite axial portions of the curved inner circumferential surface for overlapping with portions of oppositely facing end surfaces of the cap and the hub when the clip is mounted on the hub and the cap, the clip including at least one laterally outwardly extending finger engaging tab positioned adjacent one of the circumferentially spaced apart ends of the clip to facilitate removal of the clip from the hub and cap, the clip including at least one circumferentially extending through slot communicating the inner surface of the clip with an outer surface of the clip to permit flexing of the clip during removal of the clip from the hub and cap, wherein the clip includes oppositely located axial end walls each provided with an opening, the opening in one of the end walls being larger than the opening in the other end wall.

10. A retaining device for restraining axial movement between a tubular sheath, connected to a housing having an enlarged part, and a tubular dilator, connected to a hub and extending through a lumen in the housing and the sheath, the retaining device comprising:
a clip having an interior bounded by an inner circumferential surface of the clip, the clip having spaced apart circumferential ends between which is defined a clearance opening that opens into the interior of the clip for allowing the clip to be mounted on the hub and the enlarged part of the housing, the clip also having an opening at each axial end of the clip, the interior of the clip defining first and second interior portions positioned axially adjacent one another, the first interior portion being adapted to receive and circumferentially surround a portion of the hub, the second interior portion being adapted to receive and circumferentially surround a portion of the enlarged part of the housing, the first and second interior portions of the clip being of different size, wherein the first interior portion of the clip is smaller than the second interior portion of the clip.

11. The retaining device according to claim 10, wherein the clip is substantially C-shaped and possesses an outer surface that is continuously curved between the circumferential ends of the clip.

12. The retaining device according to claim 10, wherein the clip includes a plurality of circumferentially extending through slots communicating the inner circumferential surface of the clip with an outer circumferential surface of the clip.

13. The retaining device according to claim 12, wherein portions of axially adjacent ones of the through slots are circumferentially shifted relative to one another.

14. The retaining device according to claim 10, wherein the clip includes at least one circumferentially extending through slot communicating the inner circumferential surface of the clip with an outer circumferential surface of the clip.

15. The retaining device according to claim 10, wherein the opening at one axial end of the clip constitutes a first opening that opens into the first interior portion of the clip and the opening at the other axial end of the clip constitutes a second opening that opens into the second interior portion of the clip, the first opening being smaller than the second opening.

16. A retaining device for restraining axial movement between a tubular sheath, connected to a housing having an enlarged part, and a tubular dilator, connected to a hub and extending through a lumen in the housing and the sheath, the retaining device comprising:

a clip having an interior bounded by an inner circumferential surface of the clip, the clip having spaced apart circumferential ends between which is defined a clearance opening that opens into the interior of the clip for allowing the clip to be mounted on the hub and the enlarged part of the housing, the clip also having an opening at each axial end of the clip, the interior of the clip defining first and second interior portions positioned axially adjacent one another, the first interior portion being adapted to receive and circumferentially surround a portion of the hub, the second interior portion being adapted to receive and circumferentially surround a portion of the enlarged part of the housing, the first and second interior portions of the clip being of different size, wherein the opening at one axial end of the clip is smaller than the opening at the other axial end of the clip.

17. The retaining device according to claim 16, including a pair of laterally outwardly extending finger engaging tabs each located adjacent one of the circumferential ends of the clip to facilitate removal of the clip from the hub and the enlarged part of the housing.

18. A retaining device for restraining axial movement between a tubular elongated sheath, connected to a housing having an enlarged part, and a tubular dilator, connected to a hub and extending through a lumen in the housing and the sheath, the retaining device comprising:

a clip having an interior bounded by an inner circumferential surface of the clip, the clip having spaced apart circumferential ends between which is defined a clearance opening that opens into the interior of the clip for allowing the interior of the clip to receive portions of the hub and the enlarged part of the housing, the clip including at least one laterally outwardly extending finger engaging tab extending laterally outwardly from adjacent one of the circumferential ends of the clip for being engaged by an individual's finger to facilitate removal of the clip from the hub and the enlarged part of the housing, wherein the clip includes a plurality of circumferentially extending through slots communicating the inner circumferential surface of the clip with an outer circumferential surface of the clip, and wherein portions of axially adjacent ones of the through slots are circumferentially shifted relative to one another.

19. A retaining device for restraining axial movement between a tubular elongated sheath, connected to a housing having an enlarged part, and a tubular dilator, connected to a hub and extending through a lumen in the housing and the sheath, the retaining device comprising:

a clip having an interior bounded by an inner circumferential surface of the clip, the clip having spaced apart circumferential ends between which is defined a clearance opening that opens into the interior of the clip for allowing the interior of the clip to receive portions of the hub and the enlarged part of the housing, the clip including at least one laterally outwardly extending finger engaging tab extending laterally outwardly from adjacent one of the circumferential ends of the clip for being engaged by an individual's finger to facilitate removal of the clip from the hub and the enlarged part of the housing, wherein the clip has axial end walls each provided with an opening, with the opening in one axial end wall being smaller than the opening in the other axial end wall.

20. The retaining device according to claim 19, wherein the at least one laterally outwardly extending finger engaging tab includes a pair of laterally outwardly extending finger engaging tabs each positioned adjacent one of the circumferential ends of the clip.

21. The retaining device according to claim 19, wherein the clip includes a plurality of circumferentially extending through slots communicating the inner circumferential surface of the clip with an outer circumferential surface of the clip.

22. The retaining device according to claim 19, wherein the clip includes at least one circumferentially extending through slot communicating the inner circumferential surface of the clip with an outer circumferential surface of the clip.

23. The retaining device according to claim 19, wherein the opening at one axial end of the clip constitutes a first opening that opens into the first interior portion of the clip and the opening at the other axial end of the clip constitutes a second opening that opens into the second interior portion of the clip, the first opening being smaller than the second opening, the first interior portion being smaller in size than the second interior portion.

* * * * *